(12) United States Patent
Whiteman et al.

(10) Patent No.: US 7,144,597 B2
(45) Date of Patent: Dec. 5, 2006

(54) ELECTROSTATIC APPLICATION OF POWDER MATERIAL TO SOLID DOSAGE FORMS UTILIZING AN ELECTRICALLY CONDUCTIVE SHIELD

(75) Inventors: Marshall Whiteman, Ditton (GB); Martin David Hallett, Gravesend (GB); David Hoover Feather, San Diego, CA (US); Douglas Howard Nelson, Carlsbad, CA (US); Jack Michael Gazza, San Diego, CA (US)

(73) Assignee: Phoqus Pharmaceuticals Limited, Kent (GB)

( * ) Notice: Subject to any disclaimer, the term of this patent is extended or adjusted under 35 U.S.C. 154(b) by 0 days.

(21) Appl. No.: 10/501,836

(22) PCT Filed: Jan. 17, 2003

(86) PCT No.: PCT/GB03/00224

§ 371 (c)(1),
(2), (4) Date: Apr. 1, 2005

(87) PCT Pub. No.: WO03/061841

PCT Pub. Date: Jul. 31, 2003

(65) Prior Publication Data

US 2005/0208228 A1  Sep. 22, 2005

(30) Foreign Application Priority Data

Jan. 17, 2002  (GB) .................... 0201036.1

(51) Int. Cl.
*B05D 1/06* (2006.01)
*B05B 5/025* (2006.01)
(52) U.S. Cl. .............. 427/2.14; 427/466; 427/469; 427/475; 427/485; 427/118; 427/624

(58) Field of Classification Search ............... 427/2.14, 427/466, 469, 475, 485; 118/624
See application file for complete search history.

(56) References Cited

U.S. PATENT DOCUMENTS 6,475,351 B1 * 11/2002 Sun et al. ............... 204/164
6,592,671 B1 *  7/2003 Sun et al. ............... 118/625
6,724,609 B1 *  4/2004 Sun et al. ............... 361/234

FOREIGN PATENT DOCUMENTS

| JP | 2001 212479 | 8/2001 |
| WO | WO 96/35413 | 11/1996 |
| WO | WO 96/35516 | 11/1996 |
| WO | WO 98/20861 | 5/1998 |
| WO | WO 98/20863 | 5/1998 |

(Continued)

*Primary Examiner*—Fred J. Parker
(74) *Attorney, Agent, or Firm*—Patterson, Thuente, Skaar & Christensen, P.A.

(57) ABSTRACT

An apparatus for electrostatically applying a powder material to a solid dosage from includes a source (1) of charged powder material, a support assembly (2) for supporting the solid dosage form (3) with a front face in the vicinity of the source of powder material and facing the source of powder material, the support assembly (2) including an electrically conducting member (5) in the vicinity of the rear face of the solid dosage form and an electrically conducting shield (8) disposed closely around the solid dosage from (3) between the front face and the rear face of the solid dosage form, and means (4) for creating a potential difference between the source of powder material and the electrically conducting member and for maintaining the electrically conducting shield at a potential more similar to that of the source of powder material than to that of the electrically conducting member.

20 Claims, 4 Drawing Sheets

FOREIGN PATENT DOCUMENTS

| WO | WO 01/43727 | 6/2001 |
| WO | WO 02/49771 | 6/2002 |

* cited by examiner

ELECTROSTATIC APPLICATION OF POWDER MATERIAL TO SOLID DOSAGE FORMS UTILIZING AN ELECTRICALLY CONDUCTIVE SHIELD

CROSS-REFERENCE TO RELATED APPLICATIONS

Not applicable.

BACKGROUND OF THE INVENTION

1. Field of the Invention

The present invention relates to a method and apparatus for the electrostatic application of powder material onto the surfaces of solid dosage forms, and more particularly, but not exclusively, pharmaceutical solid dosage forms.

2. Description of Related Art

Including information disclosed under 37 CFR 1.97 and 1.98

A "solid dosage form" can be formed from any solid material that can be apportioned into individual units; it may be, but is not necessarily, an oral dosage form. Examples of pharmaceutical solid dosage forms include pharmaceutical tablets, pharmaceutical pessaries, pharmaceutical bougies and pharmaceutical suppositories. The term "pharmaceutical tablet" should be interpreted as covering all pharmaceutical products which are to be taken orally, including pressed tablets, pellets, capsules and spherules. Examples of non-pharmaceutical solid dosage forms include items of confectionery and washing detergent tablets.

The electrostatic application of powder material to solid dosage forms is known. In one technique, described in WO 96/35516 powder material is applied onto pharmaceutical tablets while the tablets are moving on a drum past a source of the powder material. The tablets are supported in cupped receptacles on a first drum and all the exposed areas of the tablets are coated as they pass the source of powder material. Subsequently the tablets are transferred onto a second drum where they are supported again in cupped receptacles but in the opposite orientation to that on the first drum so that areas of the tablets not exposed on the first drum are now exposed and vice versa. In that way the whole of each tablet is coated following its passage around both drums.

When using the apparatus of WO 96/35516 we have found that some powder is applied to the surface of the drum as well as to the tablet. That is wasteful of powder and also makes cleaning of the apparatus time consuming, especially if the powder being applied by the apparatus is to be charged. The coating of the sides of the tablets using the apparatus of WO 96/35516 can also be somewhat arbitrary: portions of the sides are liable to be exposed during coating on each of the drums and may therefore acquire more powder than the ends of the tablets; on the other hand, the amount of powder reaching the sides of the tablets may be limited so that even after both coating stages relatively little powder is applied to the sides of the tablet. Also, it is sometimes desired to coat only one half of the tablet (one end and part of the side wall) and in that case it is desirable to have a well defined edge to the coating. It is difficult to provide such a coating with a well defined edge using the apparatus of WO 96/35516.

BRIEF SUMMARY OF THE INVENTION

According to the invention there is provided an apparatus for electrostatically applying a powder material to a solid dosage form, the apparatus including a source of charged powder material, a support assembly for supporting the solid dosage form with a front face in the vicinity of the source of powder material and facing the source of powder material, the support assembly including an electrically conducting member in the vicinity of the rear face of the solid dosage form and an electrically conducting shield disposed closely around the solid dosage form between the front face and the rear face of the solid dosage form, and means for creating a potential difference between the source of powder material and the electrically conducting member and for maintaining the electrically conducting shield at a potential more similar to that of the source of powder material than to that of the electrically conducting member.

We have found that, by providing an electrically conducting shield closely around the solid dosage form and maintaining the shield at a potential more similar to that of the source of powder material than to that of the electrically conducting member, a physical and electrostatic barrier can be created and it becomes possible both to confine the application of powder to the solid dosage form and to coat a forward part of the solid dosage form uniformly as far as a limit defined by the shield, with substantially no coating taking place to the rear of the shield. Thus, a well defined limit to the coating can be obtained.

There can be one or more gaps in the shield extending around the solid dosage form, but it is preferred that the shield extends continuously around all of the solid dosage form.

The shape of the opening defined by the shield, in which opening the solid dosage form is received, is preferably selected according to the shape of the solid dosage form, with the shield conforming to the outline shape of the solid dosage form as seen when viewed from the source of powder material. Often that outline shape will be circular and in that case the shield preferably defines a circular opening, but it will be appreciated that other outline shapes are also possible, including, for example, an oval shape, in which case the shield preferably defines an oval opening. The shield may extend outwardly away from the vicinity of the solid dosage form. The shield preferably has a cylindrical part defining a cylindrical opening for accommodating the solid dosage form. The cylindrical opening may be of circular cross-section but, as explained above, may also have other cross-sectional shapes, for example an oval shape. The shield may consist substantially entirely of the cylindrical part. An advantage of limiting the shield to a cylindrical part closely surrounding the solid dosage form is that it reduces the effect of the shield on the electric field between the powder source and the solid dosage form. Ideally, from some points of view, the shield would have no discernible effect on that field, although in practice some effect is most likely to be discernible. The length of the cylindrical part of the shield may be relatively long, but it is preferred that the length is less than the depth of the solid dosage form, measured as the maximum separation between the front and rear faces of the solid dosage form; furthermore it is preferred that the length is substantially shorter than said depth of the solid dosage form; preferably the length is less than one third of said depth.

The provision of an electrically conducting member closely surrounding the solid dosage form over a significant area is liable to provide a degree of capacitative coupling between the shield and the solid dosage form which in turn is not desirable. Reducing the length of the shield reduces that coupling. Another feature that serves to reduce that effect is for the part of the shield immediately adjacent to the solid dosage form to have a thickness of less than 2 mm, preferably less than 1 mm. Such a small thickness may be provided by tapering of a member which may then be much thicker away from the solid dosage form, but preferably the shield is made of sheet metal. It is also preferred that the end portion of the shield adjacent to the solid dosage form and closest to the source of powder material is parallel to the side surfaces of the solid dosage form, providing a constant spacing between the end portion of the shield and the solid dosage form. It is also preferred that the edge of the end portion of the shield is at a constant spacing from the source of powder material.

In the case where the shield extends outwardly away from the vicinity of the solid dosage form it may extend radially, but alternatively it may extend outwardly in a direction inclined to a radial direction. The angle of inclination is preferably in the range of from 30 degrees to 60 degrees and may be of the order of 45 degrees. The inclination may be in a forwards direction (towards the powder source) with increasing radial distance from the solid dosage form or it may be in a rearwards direction (away from the powder source) with increasing radial distance from the solid dosage form. In the case where the inclination is in a forwards direction it is preferred that the forwardmost portions of the shield do not project forwardly as far as the forwardmost portion of the solid dosage form.

In order to improve the effectiveness of the shield as both a physical and electrical barrier, it is preferred that when, in use, the solid dosage form is supported on the support assembly, there is a gap of not more than about 1 mm, and preferably less than 1 mm, between the solid dosage form and the shield. The gap is preferably uniform around the whole of the circumference of the solid dosage form.

Preferably the electrically conducting shield comprises an electrically conducting element covered by a layer of insulating material. The provision of a layer of insulating material, which is preferably thin, prevents accidental electrical contact being made between the solid dosage form and the shield.

Preferably the electrically conducting member is adjacent to the rear face of the solid dosage form. It is not essential for the electrically conducting member to make contact with the solid dosage form but it is preferable for it to be in contact with the rear face of the solid dosage form. Preferably the electrically conducting member includes a shaped receiving portion for receiving the rear face of the solid dosage form with the rear face conforming closely to the receiving part over a major part of the area of the rear face. For example in the case where the rear face of the solid dosage form is convex, the receiving portion preferably has a corresponding concave shape.

Usually the apparatus will be arranged for applying powder material to a plurality of solid dosage forms. Thus the support assembly is preferably suitable for supporting a plurality of solid dosage forms and preferably includes a plurality of electrically conducting members, each in the vicinity of a rear face of a respective one of the solid dosage forms, and a plurality of electrically conducting shields, each disposed closely around a respective one of the solid dosage forms between the front face and the rear face of the respective solid dosage form. In such a case the plurality of shields may be formed by a single member and indeed there may be no demarcation between adjacent shields.

Preferably the support assembly is mounted for movement relative to the source of charged powder material. That enables each of the solid dosage forms to pass the source of charged powder material. The support assembly may comprise a drum rotatable about a horizontal axis, as illustrated in WO 96/35516. An alternative arrangement is to provide a body which is movable, in a translational and/or rotational movement along a path which is preferably confined to a single plane, which may be horizontal or may be inclined at an angle of up to 65 degrees to the horizontal. For example the body may travel along an endless horizontal path. The source of charged powder material may be provided above or below the horizontal path.

Preferably the means for creating a potential difference between the source of powder material and the electrically conducting member comprises a voltage source for applying a bias voltage between the source of powder material and the electrically conducting member. The invention may also be applied, however, to a case where the potential difference between the powder source and the electrically conducting member is created only by the charge on the powder, which may even be applied to the powder at a location remote from the electrically conducting member. Conveniently, the means for creating a potential difference between the source of powder material and the electrically conducting member and the means for maintaining the electrically conducting shield at a potential more similar to that of the source of powder material than to that of the electrically conducting member are provided by a single voltage source.

According to the invention there is also provided a method of electrostatically applying a powder material to a solid dosage form, the method including the steps of providing a source of charged powder material, supporting a solid dosage form on a support assembly with a front face in the vicinity of the source of powder material and facing the source of powder material, the support assembly including an electrically conducting member in the vicinity of the rear face of the solid dosage form and an electrically conducting shield disposed closely around the solid dosage form between the front face and the rear face of the solid dosage form, creating a potential difference between the source of powder material and the electrically conducting member and maintaining the shield at a potential more similar to that of the source of powder material than to that of the electrically conducting member, whereby powder material is applied to the solid dosage form forward of the shield but substantially not rearward of the shield.

The powder material may be electrostatically charged in any suitable way. For example, it may be charged triboelectrically.

The solid dosage form may be a domed tablet having a pair of opposite domed end faces joined by a cylindrical side wall. In such a case, the electrostatically charged powder material may be applied uniformly over the whole of one domed end face of the tablet and a forward part of the cylindrical side wall, the remaining, rearward, part of the cylindrical side wall being shielded from the application of powder by the shield. The solid dosage form may, more particularly, be an oral dosage form and/or a pharmaceutical dosage form, for example a pharmaceutical tablet.

The step of creating a potential difference between the source of powder material and the electrically conducting member of the support assembly may comprise the step of providing an electrically conducting roller at the powder source and applying a potential difference between the electrically conducting member of the support assembly and the electrically conducting roller at the powder source.

The potentials at which the electrically conducting shield and the source of powder material (preferably the electrically conducting roller) are preferably of the same sign and may be substantially the same.

The electrically conducting member may be electrically charged (to a potential substantially different and preferably of opposite sign to the powder source), but is preferably maintained at earth potential.

The potential difference created between the source of powder material and the electrically conducting member preferably includes a bias voltage that is a steady DC voltage. The polarity of the bias voltage is chosen according to whether the powder is positively or negatively charged, which in turn is dependent upon the powder and/or the charging process employed: for negatively charged powders the bias voltage is negative and for positively charged powders it is positive, the bias voltage being defined as positive when the potential at the source of powder material is greater than the potential at the solid dosage form and vice versa. Preferably an alternating voltage, which is preferably substantially higher than the DC voltage, is superimposed on the initial bias voltage. The presence of such an alternating voltage serves to mobilise the charged powder reducing any tendency of the powder particles to adhere to a surface on which they are carried; in a described embodiment that surface is the periphery of a roller. The alternating voltage preferably has a peak to peak value greater than, and more preferably more than twice, the peak value of the DC bias voltage. For example the alternating voltage may have a peak to peak value of the order of 5 kV. The sum of the DC bias voltage and one half of the peak to peak alternating voltage must not be so great that the potential difference causes breakdown of the air. The frequency of the alternating voltage is preferably in the range of 1 to 15 kHz.

Preferably a plurality of solid dosage forms are supported on the support assembly, the support assembly including a plurality of electrically conducting members, each in the vicinity of a rear face of a respective one of the solid dosage forms, and a plurality of electrically conducting shields, each disposed closely around a respective one of the solid dosage forms between the front face and the rear face of the respective solid dosage form, and the support assembly is moved relative to the source of charged powder material to bring in turn the front faces of the solid dosage forms into the vicinity of the source and facing the source.

Preferably, the method further comprises the step of treating the powder material to fix it on the solid dosage form. The treatment of the powder material to fix it to the solid dosage form preferably involves a heating step, preferably using infra red radiation, but other forms of heating such as convection, conduction or induction may be used. The powder material should be heated to a temperature above its softening point, and then allowed to cool until solid. It is important to control the amount of heat applied to avoid degradation of the powder material and/or the solid dosage form. The amount of heat required may be reduced by applying pressure to the powder material. Alternatively, the powder material may include a polymer which is cured during the treatment, for example, by irradiation with energy in the gamma, ultra violet or radio frequency bands.

The method may comprise the step of applying powder material to a first surface of the solid dosage form, and the subsequent step of applying powder material to a second surface of the solid dosage form. Where the method is being used to apply a continuous coating to a solid dosage form, such a step will usually be necessary if the whole surface of the dosage form is to be coated. The apparatus and method employed for applying powder material to the second surface may be similar to the apparatus and method employed for applying powder material to the first surface. Indeed the powder material may be applied to the second surface by passing the solid dosage form through the same apparatus a second time. It may be preferred, however, for the apparatus to differ from that employed for applying powder material to the first surface. For example, in the case of a domed pharmaceutical tablet, the application of powder material to an end face of the tablet may change the electrical properties of the tablet. For example the layer of applied powder material may be more electrically insulating than the material of the tablet core which may then make it desirable to increase capacitive coupling between the tablet and the electrically conducting member of the support assembly.

Preferably, the method is carried out as a continuous process.

The method of the present invention is not restricted to the use of any particular type of powder material. The powder materials described in WO 96/35413 are examples of suitable powder materials.

The powder material may include a biologically active material, that is, a material which increases or decreases the rate of a process in a biological environment. The biologically active material may be one which is physiologically active.

Conventionally, where an active material is to be administered in solid dosage form, the active material is mixed with a large volume of non-active "filler" material in order to produce a dosage form of manageable size. It has been found, however, that it is difficult to control accurately the amount of active material contained in each dosage form, leading to poor dose uniformity. That is especially the case where the required amount of active material in each dosage form is very low.

By electrostatically applying active material to a dosage form, it has been found to be possible to apply accurately very small amounts of active material to the dosage form, leading to improved dose reproducibility.

The powder material comprising active material may be applied to a solid dosage form containing the same or a different active material, or may be applied to a solid dosage form containing no active material. It should be understood that where reference is made to the solid dosage form being a pharmaceutical tablet, the term "pharmaceutical tablet" is to be taken as including a tablet core which contains no active material but is to have active material applied in the powder material. It should be understood that features described above with reference to the method of the invention may also, where appropriate be present in the apparatus of the invention and vice versa. Thus, for example, the apparatus may include one or more solid dosage forms and the dosage forms may be domed tablets as described above.

BRIEF DESCRIPTION OF THE SEVERAL VIEWS OF THE DRAWINGS

By way of example certain embodiments of the invention will now be described with reference to the accompanying drawings, in which.

DETAILED DESCRIPTION OF THE INVENTION

Figure 1:
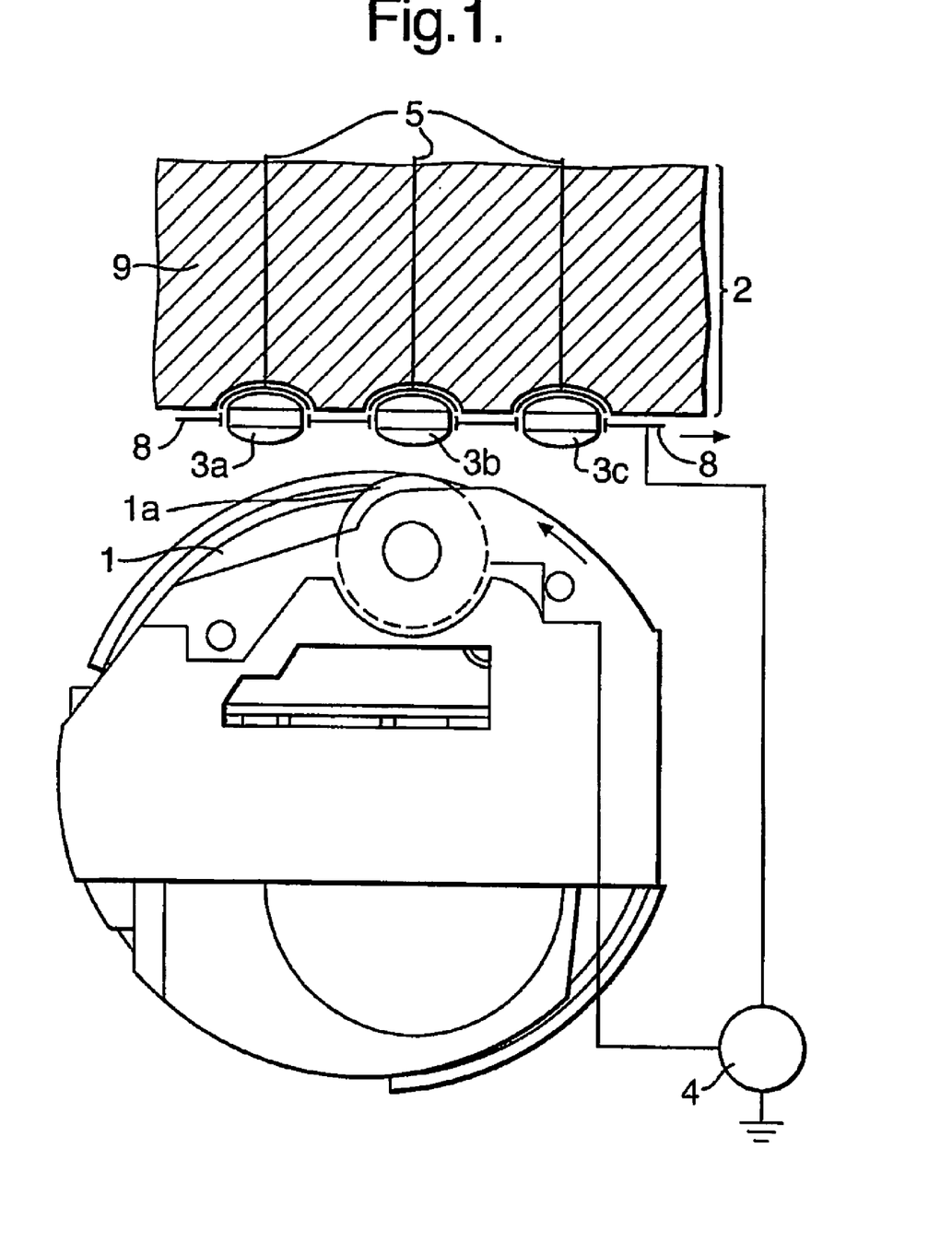
FIG. 1 is a schematic sectional view of an apparatus for electrostatically applying a powder material to a solid dosage form.
Figure 2:
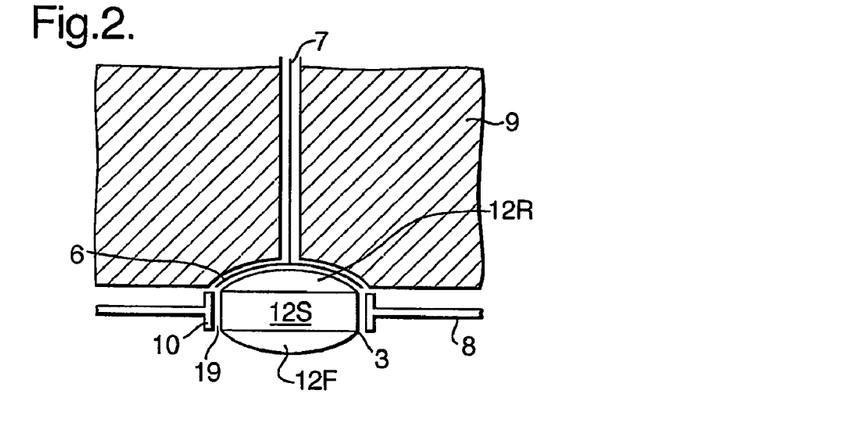
FIG. 2 is an enlarged sectional view of a part of the apparatus.
Figure 2A:
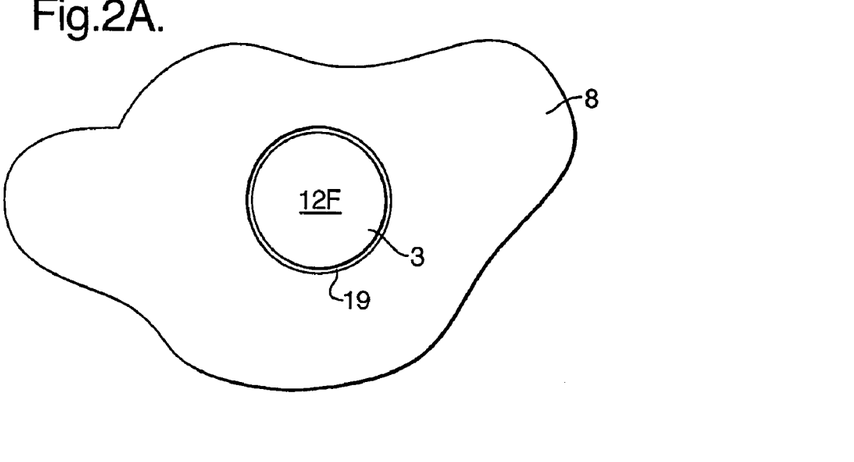
FIG. 2a is a schematic plan view of the part of the apparatus shown in FIG. 2.

Referring firstly to FIGS. 1, 2 and 2a, the apparatus shown generally comprises a source 1 of electrostatically charged powder material, a support assembly 2 for supporting tablets 3 and a voltage source 4. The support assembly 2 supports a plurality of tablets and in FIG. 1 three of the tablets 3a, 3b and 3c are shown.

The source 1 of charged powder material includes a roller 1a that is electrically conducting and is connected to the voltage source 4. Powder material in the source 1 is fed to the roller 1a and is charged triboelectrically during its passage to the roller 1a.

The support assembly 2 defines a plurality of tablet receiving stations at each of which a respective tablet 3a, 3b, 3c is received. At each station there is an electrically conducting member 5 which includes a cupped receiving part 6, on which the tablet rests, and a stem part 7. The support assembly 2 includes an electrically conducting shield 8 mounted (by suitable mounts not shown) just above an electrically insulating body 9 of the assembly 2. The shield is coated with a layer of electrically insulating material. The shield 8 has openings 19 within each of which a respective tablet 3 is received with the shield closely surrounding but spaced from the tablet 3 by a small distance (for example 0.5 mm) as shown in FIG. 2a. The shield 8 has cylindrical portions 10 of circular cross-section which define the openings 19.

Each tablet 3 has a pair of opposite domed end faces, namely a front face 12F and a rear face 12R, and also a cylindrical side wall 12S, as shown in FIG. 2. The cupped receiving part 6 of the electrically conducting member 5 is shaped so that its concave lower face matches the convex rear face 12R of the tablet 3.

It will be noted that in FIG. 1 the tablet is shown on a bottom face of the support assembly 2. It should be understood that the tablet is held on the bottom face against the force of gravity by suitable means, for example by suction (for example, by providing air passageways through the cupped receiving parts 6 and around the stem parts 7 of the conducting members 5 and connecting those passageways to the air inlet side of a vacuum pump).

The voltage source 4 applies a bias voltage to the roller 1a of the source 1 of the charged powder material and also applies the same voltage to the shield 8. The electrically conducting member 5 is earthed. The bias voltage applied by the source 4 is a steady DC bias voltage with an AC voltage superimposed thereon.

In operation of the apparatus, the tablets 3 are moved past the source 1 of electrostatically charged powder material. In FIG. 1 the tablet 3b is shown passing the roller 1a, (with the roller 1a and the tablet moving in the directions shown by the arrows in FIG. 1). The bias voltage generates an electric field between the roller 1a and the receiving part 6 of the electrically conducting member 5. That electric field causes electrostatically charged powder at the roller 1a to be transferred across to the tablet and to coat the part of the tablet that projects forwards (downwards in FIGS. 1 and 2) beyond the cylindrical portion 10 of the shield 8. The shield 8, however, provides a barrier to the powder material, preventing coating of more rearward parts of the tablet. More particularly, the shield 8 provides a physical barrier, because of its proximity to the side wall of the tablet, and also an electrostatic barrier, being at the same voltage potential as the roller 1a. Thus, the electric field, which provides the driving force for the charged powder, will be cancelled out at some point between the powder source and the shield and will be reversed in the immediate vicinity of the shield. Powder will be repelled from approaching the shield by virtue of the voltage potential of the shield and the charge on the powder.

The description above is concerned with the part of the powder coating process in which the powder is actually applied to the tablet, that being the distinctive part of the process. It will be understood, however, that there will usually be other steps in the process including in particular a step of heating the powder to fuse it and secure it to the tablet. In a case where opposite faces of a tablet are to be coated powder may be applied to the first face, that powder fused, the tablet turned over and then powder applied to the second face arid fused. Further details of other steps in the process that may be employed are given in WO 96/35516, the contents of which is incorporated herein by reference. Whilst that specification shows one particular form of support assembly for supporting and conveying the tablets, it should be understood that other systems could be used. Examples of other conveying arrangements are shown in WO 98/20861 and WO 98/20863, the contents of which are also incorporated herein by reference. Another possible conveying arrangement is one in which the tablets are conveyed along a path disposed in a single plane (which may be horizontal or inclined), travelling through various treatment stations arranged along the path. For example, powder may be applied to one face of the tablet at a first station, the powder fused at a second station, the tablet cooled at a third station, the tablet turned over at a fourth station, powder applied to the opposite face of the tablet at a fifth station, that powder fused at a sixth station and the tablet cooled at a seventh station. Suitable powder coating materials for coating the tablets are described in WO 96/35413, the contents of which is incorporated herein by reference.

Figure 3:
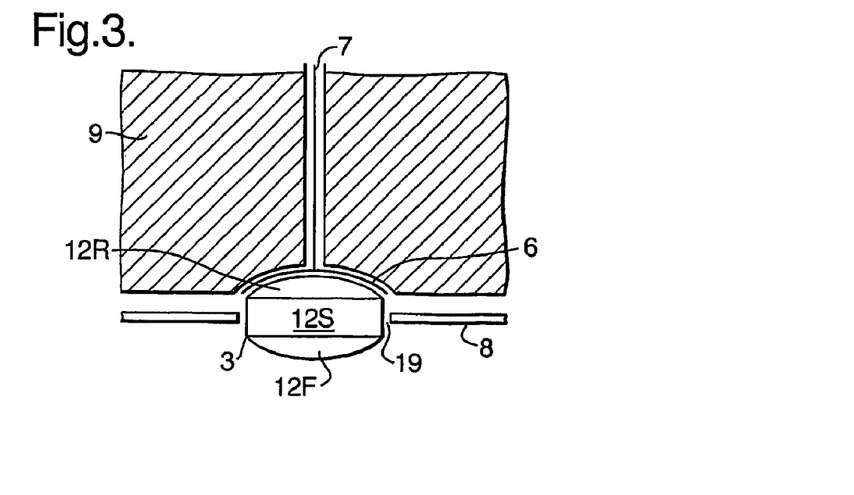
FIG. 3 is an enlarged sectional view of a modified form of the part of the apparatus shown in FIG. 2.
Figure 4A:
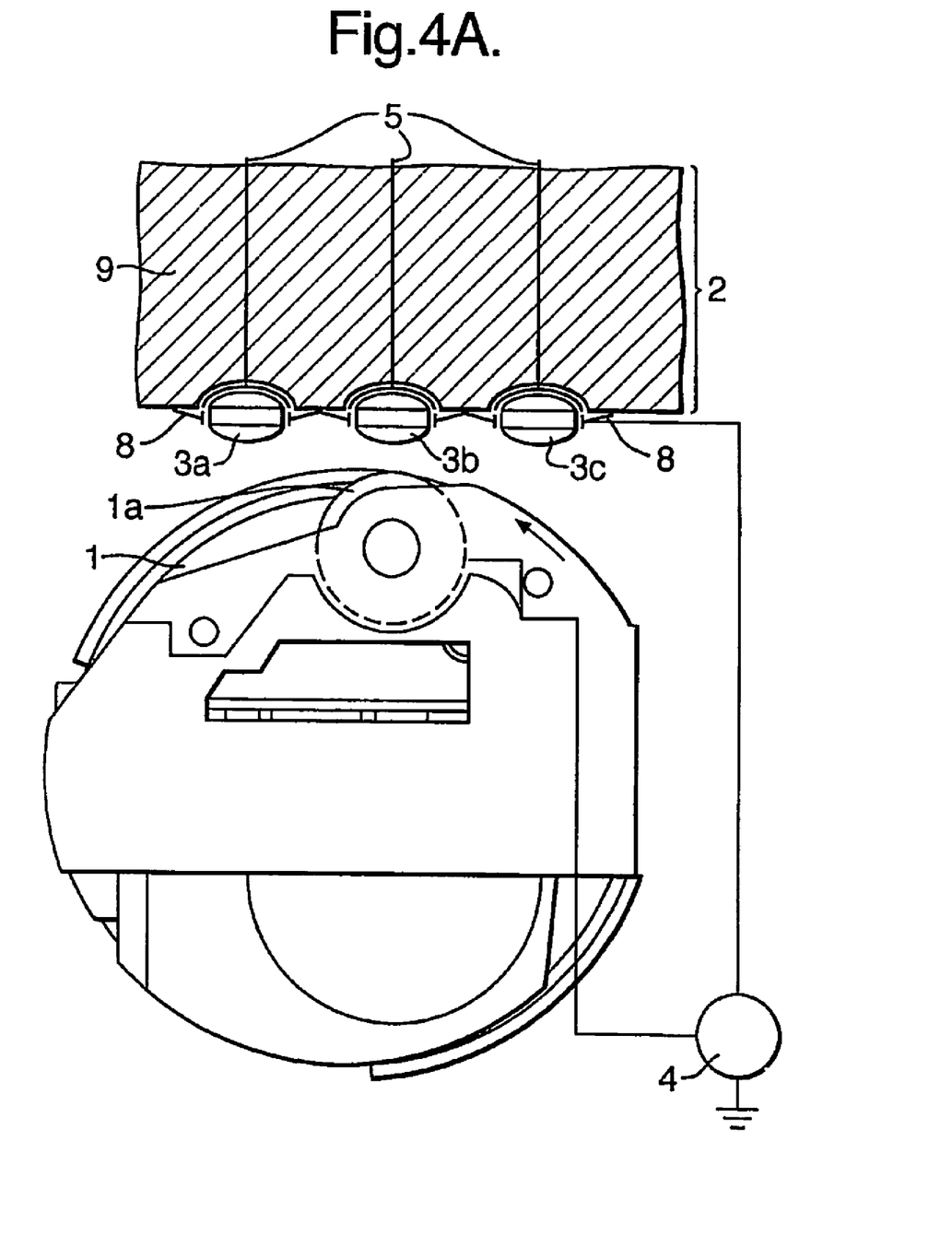
FIG. 4a is a schematic sectional view of another apparatus for electrostatically applying a powder material to a solid dosage form.
Figure 4B:
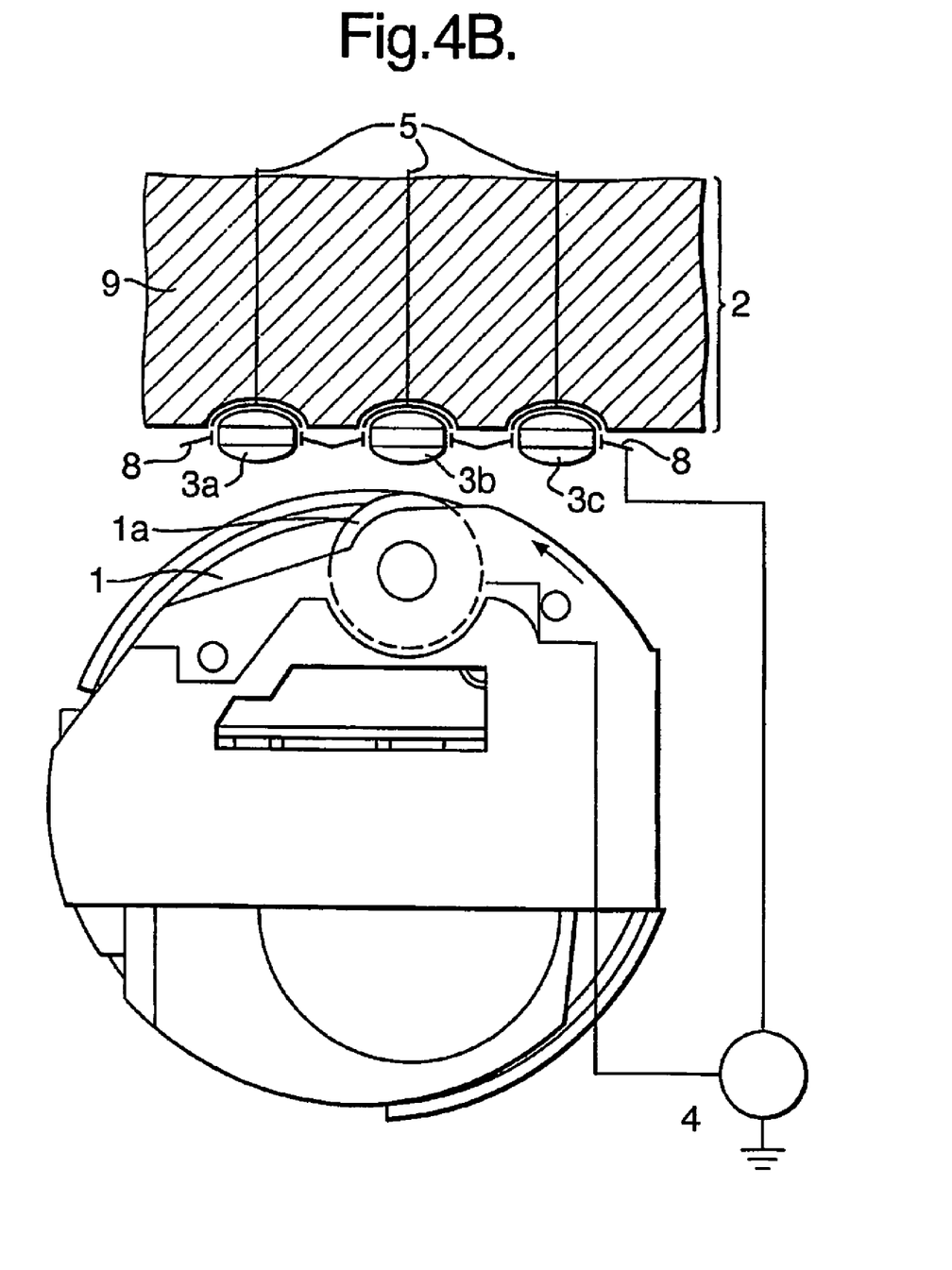
FIG. 4b is a schematic sectional view of yet another apparatus for electrostatically applying a powder material to a solid dosage form.

Whilst FIGS. 1, 2 and 2a describe one particular shield arrangement for applying powder to a tablet, it should be understood that the shield may take any of a wide variety of forms. For example FIG. 3 shows an arrangement that is the same as that shown in FIGS. 1, 2 and 2a but in which the shield 8 is in the form of a flat metal sheet with circular openings 19 within which the tablets 3 are received. The shield of FIG. 3 has the advantage that there is relatively little capacitance between the shield and each tablet 3 because only the edge of the sheet is close to the tablet. FIG. 4a shows an arrangement similar to that of FIG. 3, but in this case the shield 8 is inclined upwardly and radially outwardly from each tablet. FIG. 4b shows a similar arrangement to that of FIG. 4a but in this case the shield 8 is inclined downwardly and radially outwardly from each tablet. It will be understood that other shapes of shield can also be adopted.

In the illustrated embodiments the body 9 is described as electrically insulating, but it is also possible for the body 9 to be electrically conducting, provided that it is insulated from the shield 8. If the body 9 is electrically conducting, then there is no longer a need to provide the separate electrically conducting members 5.

Whilst in the described embodiment the shield 8 and the roller 1a are maintained at the same potential and connected to the same voltage source, that need not be the case. For example, the shield 8 could be maintained at a potential of the same polarity as, but a different (typically smaller) magnitude from, the potential of the roller 1a. The potential at which the shield 8 is maintained may also be made adjustable to enable the effect of the shield on the coating of the tablet to be altered.

The invention claimed is:

1. An apparatus for electrostatically applying a powder material to a solid dosage form having a front face and a rear face, the apparatus comprising:

a source of charged powder material;

a support assembly for supporting the solid dosage form with the front face in the vicinity of the source of charged powder material and facing the source of charged powder material, the support assembly comprising an electrically conducting member in the vicinity of the rear face of the solid dosage form and an electrically conducting shield disposed around the solid dosage form between the front face and the rear face of the solid dosage form; and means for creating a potential difference between the source of charged powder material and the electrically conducting member and for maintaining the electrically conducting shield at a potential more similar to that of the source of powder material than to that of the electrically conducting member.

2. An apparatus according to claim 1, wherein the electrically conducting shield extends continuously around all of the solid dosage form.

3. An apparatus according to claim 1, wherein the electrically conducting shield has a cylindrical part defining a cylindrical opening for accommodating the solid dosage form.

4. An apparatus according to claim 3, wherein the length of the cylindrical part of the electrically conducting shield is less than the depth of the solid dosage form, measured as the maximum separation between the front and rear faces of the solid dosage form.

5. An apparatus according to claim 1, wherein during use, the solid dosage form is supported on the support assembly and there is a gap of not more than about 1 mm between the solid dosage form and the shield.

6. An apparatus according to claim 1, wherein the electrically conducting shield comprises an electrically conducting element covered by a layer of insulating material.

7. An apparatus according to claim 1, wherein the electrically conducting member is adjacent to the rear face of the solid dosage form.

8. An apparatus according to claim 7, wherein the electrically conducting member includes a shaped receiving part for receiving the rear face of the solid dosage form, with the rear face conforming closely to the receiving part over a major part of the area of the rear face.

9. An apparatus according to claim 1, wherein the potentials at which the electrically conducting shield and the source of powder material are maintained are of the same sign.

10. An apparatus according to claim 1, wherein the electrically conducting member is arranged to be maintained at earth potential.

11. An apparatus according to claim 1, wherein the support assembly is suitable for supporting a plurality of solid dosage forms and comprises a plurality of electrically conducting members, each in the vicinity of a rear face of a respective one of the solid dosage forms, and a plurality of electrically conducting shields, each disposed around a respective one of the solid dosage forms between the front face and the rear face of the respective solid dosage form.

12. An apparatus according to claim 1, wherein the means for creating a potential difference between the source of powder material and the electrically conducting member comprises a voltage source for applying a bias voltage between the source of powder material and the electrically conducting member.

13. An apparatus according to claim 1, wherein the electrically conducting shield is disposed closely around the solid dosage form between the front face and the rear face of the solid dosage form.

14. An apparatus for electrostatically applying a powder material to solid dosage forms each having a front face and a rear face, the apparatus comprising:

a source of charged powder material;

a support assembly for supporting the solid dosage forms with front faces of the solid dosage forms in the vicinity of the source of charged powder material and facing the source of charged powder material, the support assembly comprising an electrically conducting member in the vicinity of the rear faces of the solid dosage forms and an electrically conducting shield disposed around the solid dosage forms between the front faces and the rear faces of the solid dosage forms, the shield including a plurality of openings for receiving respective solid dosage forms; and means for creating a potential difference between the source of charged powder material and the electrically conducting member and for maintaining the electrically conducting shield at a potential more similar to that of the source of powder material than to that of the electrically conducting member.

15. A method of electrostatically applying a powder material to a solid dosage form having a front face and a rear face, the method comprising the steps of:

providing a source of charged powder material:

supporting a solid dosage form on a support assembly with the front face in the vicinity of the source of charged powder material and facing the source of charged powder material, the support assembly comprising an electrically conducting member in the vicinity of the rear face of the solid dosage form and an electrically conducting shield disposed around the solid dosage form between the front face and the rear face of the solid dosage form;

creating a potential difference between the source of charged powder material and the electrically conducting member; and maintaining the shield at a potential more similar to that of the source of powder material than to that of the electrically conducting member, whereby powder material is applied to the solid dosage form forward of the shield but substantially not rearward of the shield.

16. A method according to claim 15, wherein the solid dosage form is a domed tablet having a pair of opposite domed end faces joined by a cylindrical side wall.

17. A method according to claim 16, wherein the electrically conducting shield is disposed closely around the cylindrical side wall, and powder material is applied to the part of the side wall forward of the shield but not to the part of the side wall rearward of the shield.

18. A method according to claim 15, wherein the potential difference created between the source of powder material and the electrically conducting member includes a bias voltage that is a steady DC voltage.

19. A method according to claim 15, wherein an alternating voltage is superimposed on the DC voltage.

20. A method according to claim 15, further comprising the step of treating the powder material to fix it on the solid dosage form.

* * * * *